(12) United States Patent
Fukumoto et al.

(10) Patent No.: US 12,129,445 B2
(45) Date of Patent: Oct. 29, 2024

(54) FLUORINE-CONTAINING ETHER COMPOUND, LUBRICANT FOR MAGNETIC RECORDING MEDIUM, AND MAGNETIC RECORDING MEDIUM

(71) Applicant: Resonac Corporation, Tokyo (JP)

(72) Inventors: Naoya Fukumoto, Ichihara (JP); Daisuke Yagyu, Ichihara (JP); Tsuyoshi Kato, Ichihara (JP); Katsumi Murofushi, Tokyo (JP)

(73) Assignee: Resonac Corporation, Tokyo (JP)

( * ) Notice: Subject to any disclaimer, the term of this patent is extended or adjusted under 35 U.S.C. 154(b) by 0 days.

(21) Appl. No.: 17/630,639

(22) PCT Filed: Jul. 9, 2020

(86) PCT No.: PCT/JP2020/026883
§ 371 (c)(1),
(2) Date: Jan. 27, 2022

(87) PCT Pub. No.: WO2021/020066
PCT Pub. Date: Feb. 4, 2021

(65) Prior Publication Data
US 2022/0259513 A1 Aug. 18, 2022
US 2024/0034951 A2 Feb. 1, 2024

(30) Foreign Application Priority Data
Jul. 31, 2019 (JP) .................. 2019-141291

(51) Int. Cl.
C10M 107/38 (2006.01)
C07C 43/13 (2006.01)
(Continued)

(52) U.S. Cl.
CPC ......... *C10M 107/38* (2013.01); *C07C 43/137* (2013.01); *C08G 65/3312* (2013.01);
(Continued)

(58) Field of Classification Search
CPC .......... C10M 107/38; C10M 2213/043; C10M 2213/0606; G11B 5/725; G11B 5/7253
See application file for complete search history.

(56) References Cited

U.S. PATENT DOCUMENTS 11,332,686 B2 * 5/2022 Fukumoto ............ G11B 5/7257
2012/0225217 A1 9/2012 Itoh et al.
(Continued)

FOREIGN PATENT DOCUMENTS

JP 4632144 B2 2/2011
JP 2012-009090 A 1/2012
(Continued)

OTHER PUBLICATIONS

Guo, X.-C., et al., "A multidentate lubricant for use in hard disk drives at sub-nanometer thickness", J. Appl. Phys., 2012, 111, 024503.
(Continued)

*Primary Examiner* — Holly Rickman
*Assistant Examiner* — Linda N Chau
(74) *Attorney, Agent, or Firm* — Sughrue Mion, PLLC

(57) ABSTRACT

A fluorine-containing ether compound represented by the following formula (1) is provided.

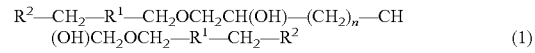

(in the formula (1), n is an integer of 2 to 6, $R^1$ is a perfluoropolyether chain, $R^2$ is —OCH$_2$CH(OH)CH$_2$O(CH$_2$)$_m$OH (m in the formula is an integer of 2 to 4)).

16 Claims, 1 Drawing Sheet

(51) Int. Cl.
  *C08G 65/331* (2006.01)
  *G11B 5/725* (2006.01)
  *C10N 40/18* (2006.01)
  *C10N 50/00* (2006.01)

(52) U.S. Cl.
  CPC ........ *C08G 65/3318* (2013.01); *G11B 5/7253* (2020.08); *C10M 2213/0606* (2013.01); *C10N 2040/18* (2013.01); *C10N 2050/025* (2020.05)

(56) References Cited

U.S. PATENT DOCUMENTS

| | | |
|---|---|---|
| 2012/0315504 A1 | 12/2012 | Shimizu et al. |
| 2016/0068778 A1 | 3/2016 | Conley et al. |
| 2017/0260472 A1 | 9/2017 | Sagata et al. |
| 2020/0002258 A1 | 1/2020 | Fukumoto et al. |

FOREIGN PATENT DOCUMENTS

| | | |
|---|---|---|
| JP | 2013-018961 A | 1/2013 |
| WO | 2013/054393 A1 | 4/2013 |
| WO | 2016/084781 A1 | 6/2016 |
| WO | 2018/147017 A1 | 8/2018 |
| WO | 2018/159250 A1 | 9/2018 |
| WO | 2021/024585 A1 | 2/2021 |

OTHER PUBLICATIONS

International Search Report of PCT/JP2020/026883 dated Sep. 8, 2020 [PCT/ISA/210].

\* cited by examiner

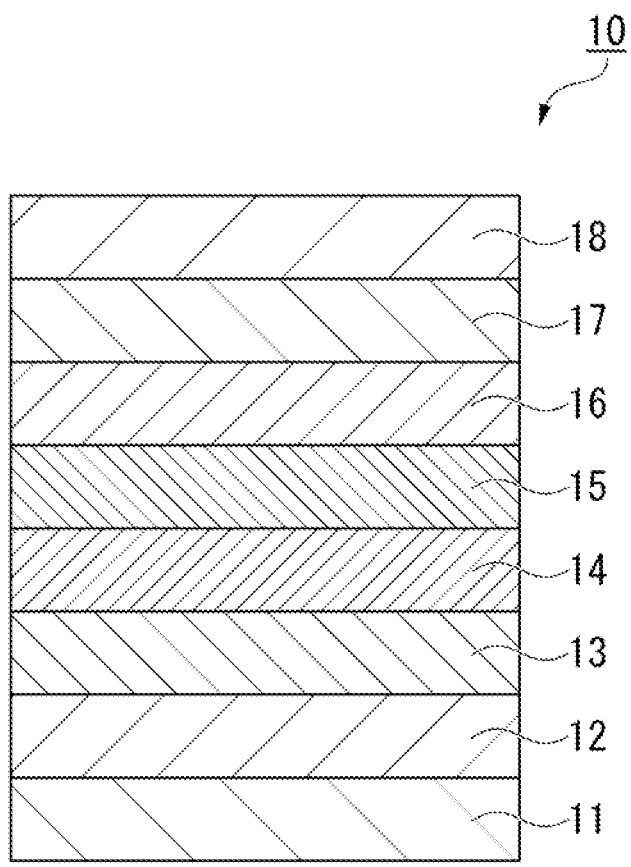

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2020/026883, filed Jul. 9, 2020, claiming priority to Japanese Patent Application No. 2019-141291, filed Jul. 31, 2019, the contents of all of which are incorporated herein by reference in their entirety.

TECHNICAL FIELD

The present invention relates to a fluorine-containing ether compound preferable for application as a lubricant for magnetic recording media, a lubricant for a magnetic recording medium containing the same, and a magnetic recording medium.

BACKGROUND ART

Development of magnetic recording media suitable for a high recording density is underway to improve the recording density of magnetic recording/reproducing devices.

Conventionally, there have been magnetic recording media having a recording layer formed on a substrate and a protective layer made of carbon or the like formed on the recording layer. The protective layer protects information recorded in the recording layer and enhances the sliding properties of a magnetic head. However, the protective layer provided on the recording layer is not sufficient for magnetic recording media to obtain sufficient durability. Therefore, it is common to form a lubricating layer on the surface of the protective layer by applying a lubricant.

As the lubricant that is used at the time of forming the lubricating layer in magnetic recording media, for example, lubricants containing a compound having a polar group such as a hydroxy group at a terminal of a fluorine-based polymer having a repeating structure containing $CF_2$ have been proposed.

For example, Patent Document 1 discloses a fluoropolyether compound wherein two or more perfluoropolyethers are bonded by ether bonds respectively to an aliphatic hydrocarbon chain having 4 to 10 carbon atoms which is located at the center of a molecule thereof.

In addition, Patent Document 2 discloses a compound in which a substituent is disposed in which a plurality of hydroxyl groups are present at both terminal portions and the shortest distance between the hydroxyl groups is three atoms or more.

CITATION LIST

Patent Document

[Patent Document 1]
International Publication WO 2016/084781
[Patent Document 2]
Japanese Patent No. 4632144

SUMMARY OF INVENTION

Technical Problem

There is a demand for a further decrease in the flying height of a magnetic head in magnetic recording/reproducing devices. This requires a further decrease in the thickness of lubricating layers in magnetic recording media.

However, ordinarily, there is a tendency that a decrease in the thickness of lubricating layers degrades the coatability of lubricating layers and thereby degrades the wear resistance of magnetic recording media. In addition, when the thickness of a lubricating layer is made thinner and adhesion between a protective layer and the lubricating layer which coats the surface of the protective layer is decreased to suppress a decrease in wear resistance, pickup, which is the adhesion of a fluorine-containing ether compound included in a lubricating layer to a magnetic head, tends to occur.

The present invention has been made in consideration of the above-described circumstances, and an objective of the present invention is to provide a fluorine-containing ether compound that is capable of forming lubricating layers, which have excellent wear resistance and can prevent pickup in spite of a thin thickness, and can be preferably used as a material for lubricants for magnetic recording media.

In addition, another objective of the present invention is to provide a lubricant for a magnetic recording medium containing the fluorine-containing ether compound of the present invention.

In addition, still another objective of the present invention is to provide a magnetic recording medium having a lubricating layer containing the fluorine-containing ether compound of the present invention and having excellent reliability and durability.

Solution to Problem

The present inventors repeated intensive studies to solve the above-described problem.

As a result, the present inventors found that a fluorine-containing ether compound in which a perfluoropolyether chain is bonded to both terminals of a chain structure, which consists of 2 to 6 methylene groups (—$CH_2$—), via a linking group including a hydroxy group, and a terminal group represented by —$OCH_2CH(OH)CH_2O(CH_2)_mOH$ (m in the formula is an integer of 2 to 4) is further bonded to a terminal of the perfluoropolyether chain via a methylene group (—$CH_2$—), is preferable and obtained the idea of the present invention.

That is, the present invention relates to the following matters.

A compound of a first aspect of the present invention is the following compound.

[1] A fluorine-containing ether compound represented by the following formula (1).

$$R^2—CH_2—R^1—CH_2OCH_2CH(OH)—(CH_2)_n—CH(OH)CH_2OCH_2—R^1—CH_2—R^2 \quad (1)$$

(In the formula (1), n is an integer of 2 to 6, $R^1$ is a perfluoropolyether chain, $R^2$ is —$OCH_2CH(OH)CH_2O(CH_2)_mOH$ (m in the formula is an integer of 2 to 4).)

The compound of the first aspect of the present invention preferably has characteristics to be described in the following [2] to [4]. Two or more of the following characteristics are also preferably combined together.

[2] The fluorine-containing ether compound according to [1], in which $R^1$ in the formula (1) is represented by any one of the following formulae (2) to (4).

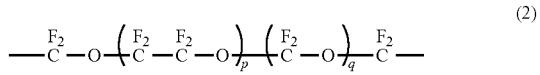

-continued

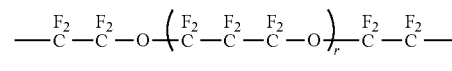
(3)

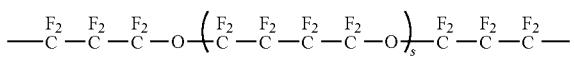
(4)

(In the formula (2), p represents 1 to 30, and q represents 0 to 30.)

(In the formula (3), r represents 1 to 30.)

(In the formula (4), s represents 1 to 20.)

[3] The fluorine-containing ether compound according to [1] that is any one of compounds represented by the following formulae (A) to (F).

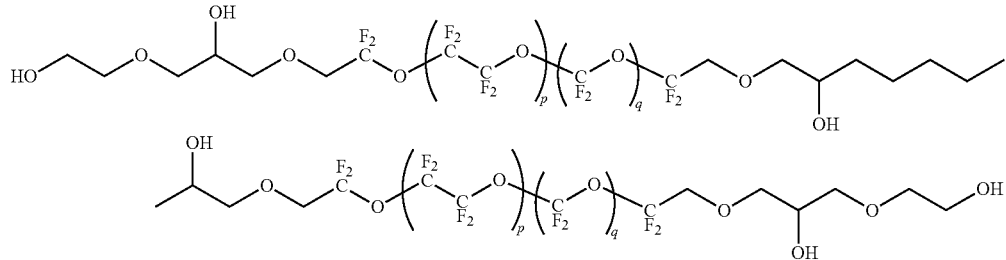
(A)

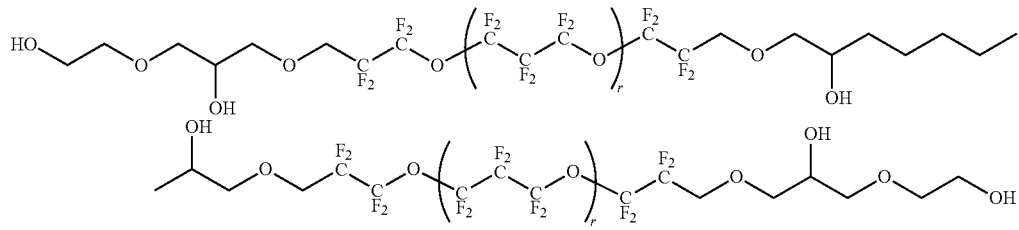
(B)

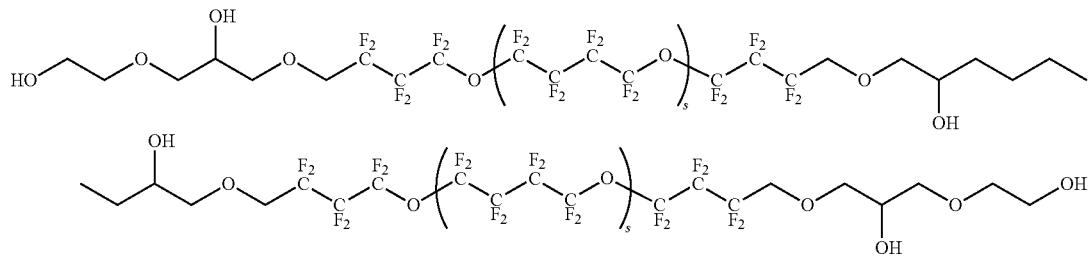
(C)

(In the formula (A), p represents 1 to 30, and q represents 0 to 30.)

(In the formula (B), r represents 1 to 30.)

(In the formula (C), s represents 1 to 20.)

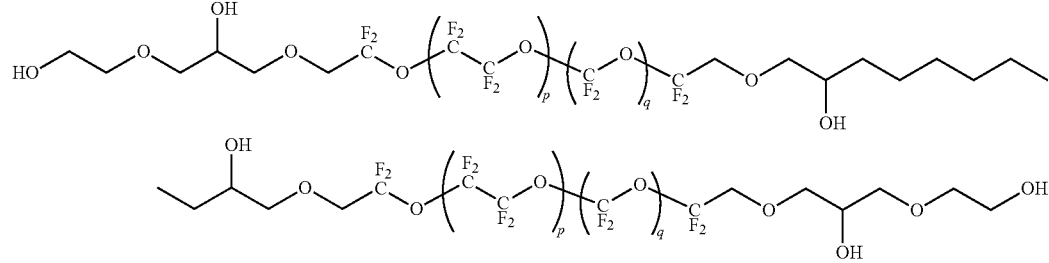
(D)

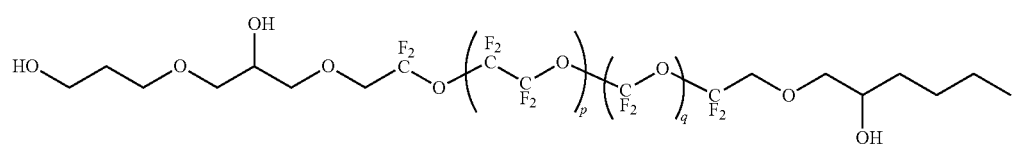
(E)

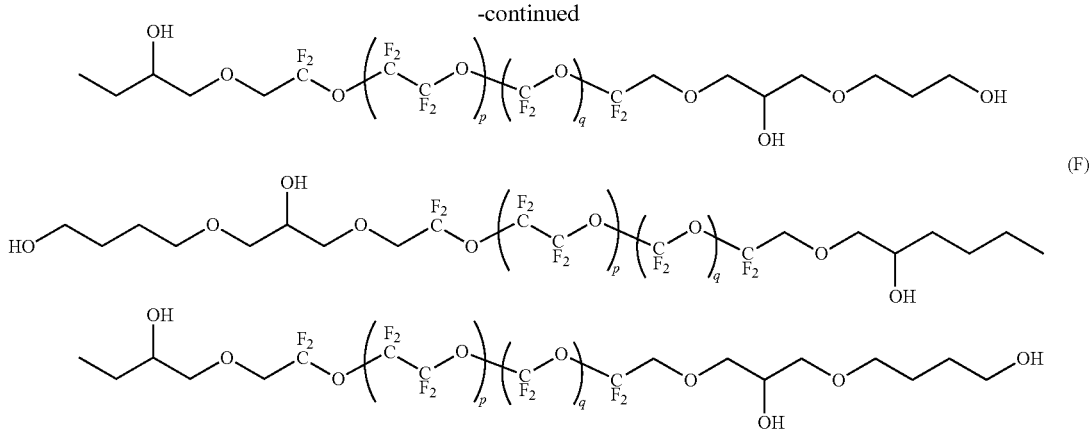

(F)

(In the formula (D), p represents 1 to 30, and q represents 0 to 30.)

(In the formula (E), p represents 1 to 30, and q represents 0 to 30.)

(In the formula (F), p represents 1 to 30, and q represents 0 to 30.)

[4] The fluorine-containing ether compound according to any one of [1] to [3], in which a number-average molecular weight thereof is in a range of 500 to 10000.

A second aspect of the present invention is the following lubricant for a magnetic recording medium.

[5] A lubricant for a magnetic recording medium containing the fluorine-containing ether compound according to any one of [1] to [4].

A third aspect of the present invention is the following magnetic recording medium.

[6] A magnetic recording medium including at least a magnetic layer, a protective layer and a lubricating layer sequentially provided on a substrate, in which the lubricating layer contains the fluorine-containing ether compound according to any one of [1] to [4].

[7] The magnetic recording medium according to [6], in which the lubricating layer has an average film thickness of 0.5 nm to 3 nm.

Advantageous Effects of Invention

The fluorine-containing ether compound of the present invention is preferably used as a material for lubricants for magnetic recording media.

The lubricant for a magnetic recording medium of the present invention contains the fluorine-containing ether compound of the present invention and is thus capable of forming lubricating layers capable of obtaining excellent wear resistance and preventing pickup, in spite of a thin thickness.

The magnetic recording medium of the present invention is provided with a lubricating layer which has excellent wear resistance and can prevent pickup, and thus has excellent reliability and durability.

BRIEF DESCRIPTION OF DRAWINGS

The FIGURE is a schematic cross-sectional view showing a preferable example of an embodiment of a magnetic recording medium of the present invention.

DESCRIPTION OF EMBODIMENTS

Hereinafter, a fluorine-containing ether compound, a lubricant for a magnetic recording medium (hereinafter, abbreviated as "lubricant" in some cases) and a magnetic recording medium of the present invention will be described in detail. The present invention is not limited only to an embodiment to be described below.

The present embodiment is simply a specific description for better understanding of the gist of the invention and does not limit the present invention unless particularly otherwise specified. Numerical values, orders, times, ratios, materials, amounts, configurations and the like can be modified, added, omitted, substituted and the like within the scope of the gist of the present invention.

[Fluorine-Containing Ether Compound]

A fluorine-containing ether compound of the present embodiment is represented by the following formula (1).

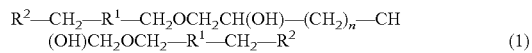

(In the formula (1), n is an integer of 2 to 6, $R^1$ is a perfluoropolyether chain, $R^2$ is $-OCH_2CH(OH)CH_2O(CH_2)_mOH$ (m in the formula is an integer of 2 to 4).)

Here, the reason that excellent wear resistance can be obtained and pickup is prevented in spite of a thin thickness in a case where a lubricating layer is formed on a protective layer of a magnetic recording medium using a lubricant containing the fluorine-containing ether compound of the present embodiment will be described.

As shown in the formula (1), the fluorine-containing ether compound of the present embodiment has two perfluoropolyether chains represented by $R^1$ (hereinafter, abbreviated as "PFPE chain" in some cases). The PFPE chain coats the surface of a protective layer and also imparts lubricity to a lubricating layer to reduce a friction force between a magnetic head and the protective layer when the lubricating layer is formed by applying a lubricant containing the fluorine-containing ether compound onto the protective layer.

In addition, in the fluorine-containing ether compound represented by the formula (1), a linking group ($-CH(OH)CH_2OCH_2-$) including a hydroxy group ($-OH$) is bonded respectively to both terminals of a hydrocarbon chain ($-(CH_2)_n-$, (n in the formula is an integer of 2 to 6)), which consists of 2 to 6 methylene groups and is located at the center of a molecule thereof. The hydroxy group contributes to an improvement of adhesion between a protective layer and a fluorine-containing ether compound included in the lubricating layer, and the distance between a hydroxy group included in one linking group and a hydroxy group included in the other linking group is appropriate due to the hydrocarbon chain located between the two linking groups. In addition, as the two linking groups including a hydroxy group include an ether bond (—O—), the fluorine-containing ether compound has appropriate hardness. Therefore, lubricating layers having excellent coatability and wear resistance can be obtained by using a lubricant containing the fluorine-containing ether compound represented by the formula (1).

In addition, as shown in the formula (1), a terminal group represented by $R^2$ is respectively bonded to a terminal of the two PFPE chains represented by $R^1$ wherein the terminal is located on the opposite side of the linking group including a hydroxyl group. The terminal group represented by $R^2$ is —OCH$_2$CH(OH)CH$_2$O(CH$_2$)$_m$OH (m in the formula is an integer of 2 to 4). Two hydroxy groups (—OH) that are included in each of the two terminal groups represented by $R^2$ closely attach the fluorine-containing ether compound and the protective layer in the lubricating layer containing the fluorine-containing ether compound of the present embodiment, and thereby suppress pickup.

In the terminal group represented by $R^2$, the two hydroxy groups bond to different carbon atoms respectively, and the carbon atoms to which the hydroxy groups bond are bonded to each other through a linking group including an oxygen atom (a linking group including —O— (ether bond)). The linking group including the ether bond imparts flexibility to the terminal group represented by $R^2$. Therefore, compared with, for example, a fluorine ether compound in which two hydroxy groups that are included in a terminal group bond to different carbon atoms, and the carbon atoms to which the hydroxy groups bond are bonded to each other, the lubricating layer containing the fluorine-containing ether compound of the present embodiment is easily adsorbed to the protective film and is excellent in terms of adhesion between the lubricating layer and the protective layer.

From this fact, it is assumed that a lubricant containing the fluorine-containing ether compound of the present embodiment is capable of coating the surface of the protective layer at a high coating rate in spite of a thin thickness and capable of forming a lubricating layer which has excellent wear resistance and can suppress pickup.

In the fluorine-containing ether compound of the present embodiment represented by the formula (1), $R^1$ is the perfluoropolyether chain (PFPE chain), and two $R^1$ included in the fluorine-containing ether compound represented by the formula (1) are the same.

$R^1$ is not particularly limited and can be appropriately selected depending on performance or the like required for lubricants containing the fluorine-containing ether compound.

$R^1$ is preferably represented by any one of the following formula (2) to formula (4). In a case where $R^1$ is represented by any one of the formula (2) to formula (4), the synthesis of the fluorine-containing ether compound is easy, which is preferable.

In addition, in a case where $R^1$ is represented by any one of the formula (2) to formula (4), the ratio of the number of oxygen atoms (the number of the ether bonds (—O—)) to the number of carbon atoms in the perfluoropolyether chain is appropriate. Therefore, a fluorine-containing ether compound having appropriate hardness is obtained. Therefore, the fluorine-containing ether compound applied onto the protective layer is less likely to aggregate on the protective layer, and it is possible to form a lubricating layer having a thinner thickness at a sufficient coating rate. In addition, in a case where $R^1$ is represented by any one of the formula (2) to formula (4), the fluorine-containing ether compound becomes capable of providing lubricating layers having favorable wear resistance.

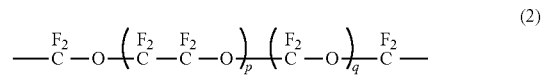

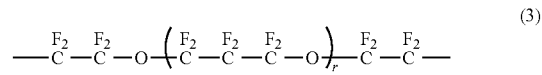

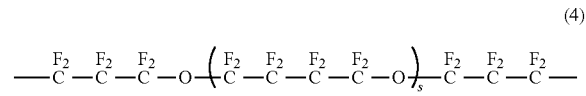

(In the formula (2), p represents 1 to 30, and q represents 0 to 30.)

(In the formula (3), r represents 1 to 30.)

(In the formula (4), s represents 1 to 20.)

In the formula (2), the arrangement sequence of (CF$_2$—CF$_2$—O) and (CF$_2$—O), which are repeating units, is not particularly limited. In the formula (2), the number p of (CF$_2$—CF$_2$—O)'s and the number q of (CF$_2$—O)'s may be equal to each other or may be different from each other. The formula (2) may include any of a random copolymer, a block copolymer, and an alternating copolymer composed of the monomer units (CF$_2$—CF$_2$—O) and (CF$_2$—O).

In a case where $R^1$ in the formula (1) is the formula (2), p that indicates the average degree of polymerization is 1 to 30, preferably 1 to 20 and more preferably 1 to 15. p may be 3 to 7 or 7 to 13 as necessary. In a case where $R^1$ in the formula (1) is the formula (2), q that indicates the average degree of polymerization is 0 to 30, preferably 0 to 20 and more preferably 0 to 15. q may be 3 to 7 or 7 to 13 as necessary. In addition, in a case where q is 0, p is preferably 1 to 17.

In a case where r that indicates the average degree of polymerization is 1 to 30 in the formula (3), the number-average molecular weight of the fluorine-containing ether compound of the present embodiment is likely to be within a preferable range. r is preferably 2 to 20 and more preferably 3 to 10.

In a case where s that indicates the average degree of polymerization is 1 to 20 in the formula (4), the number-average molecular weight of the fluorine-containing ether compound of the present embodiment is likely to be within a preferable range. s is preferably 2 to 15 and more preferably 2 to 8.

In a case where n is an integer of 2 to 6, the distance between the hydroxy groups which are present at both terminals of the hydrocarbon chain, which consists of methylene groups and is located at the center of a molecule, is in an appropriate range. The aforementioned n is preferably 4 to 6 as the distance between the hydroxy groups becomes more appropriate.

In the formula (1), $R^2$ is —OCH$_2$CH(OH)CH$_2$O(CH$_2$)$_m$OH (m in the formula is an integer of 2 to 4).

The fluorine-containing ether compound represented by the formula (1) is, specifically, preferably any one of the compounds represented by the formulae (A) to (F). p, q, r and s in the formulae (A) to (F) are values indicating the average degree of polymerization and thus do not necessarily need to be integers.

In the compound represented by the formula (A), n is 4, $R^1$ is the formula (2), and m in $R^2$ is 2.

In the compound represented by the formula (B), n is 4, $R^1$ is the formula (3), and m in $R^2$ is 2.

In the compound represented by the formula (C), n is 4, $R^1$ is the formula (4), and m in $R^2$ is 2.

In the compound represented by the formula (D), n is 6, $R^1$ is the formula (2), and m in $R^2$ is 2.

In the compound represented by the formula (E), n is 4, $R^1$ is the formula (2), and in in $R^2$ is 3.

In the compound represented by the formula (F), n is 4, $R^1$ is the formula (2), and m in $R^2$ is 4.

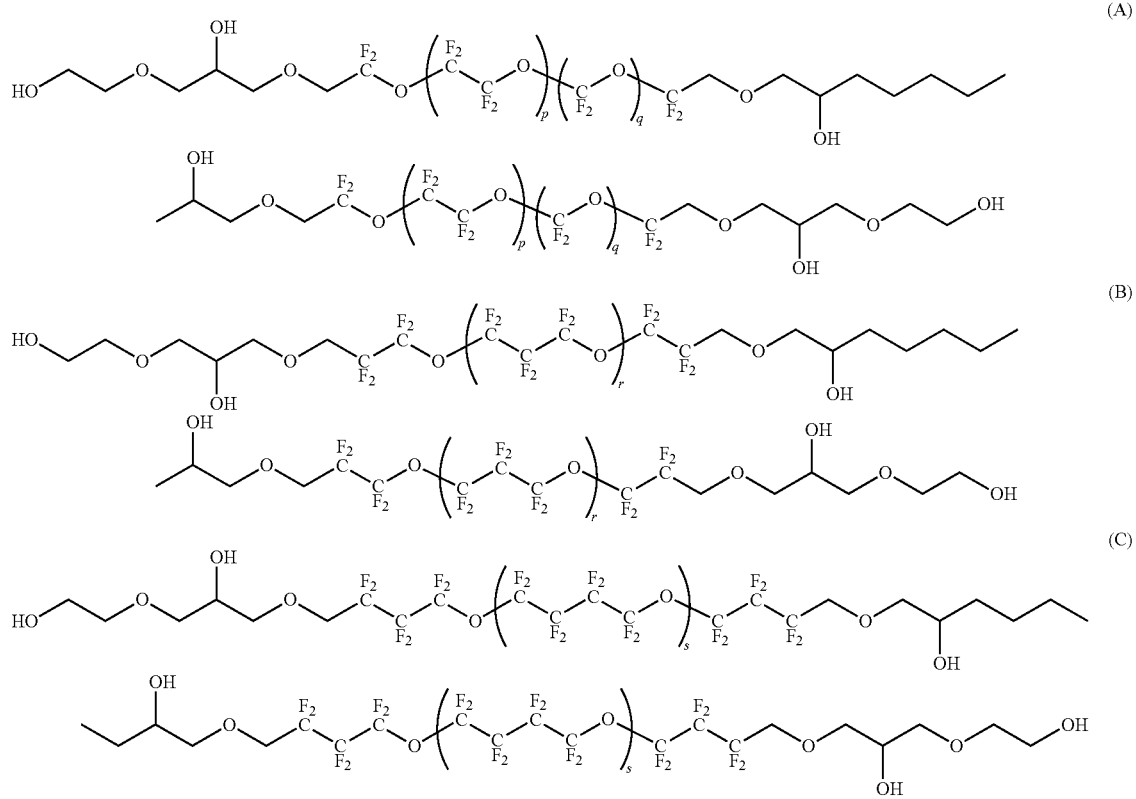

(In the formula (A), p represents 1 to 30, and q represents 0 to 30.)

(In the formula (B), r represents 1 to 30.)

(In the formula (C), s represents 1 to 20.)

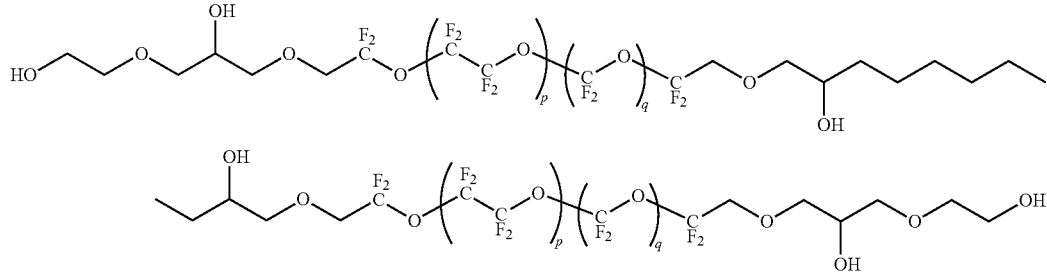

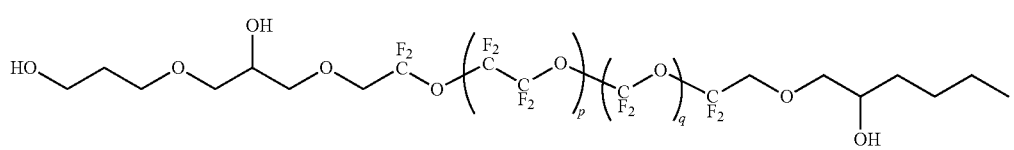

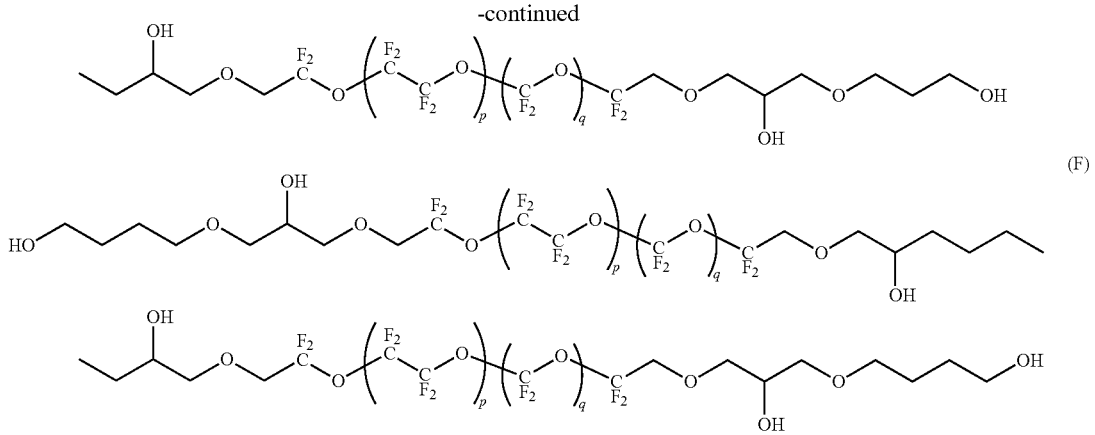

(F)

(In the formula (D), p represents 1 to 30, and q represents 0 to 30.)

(In the formula (E), p represents 1 to 30, and q represents 0 to 30.)

(In the formula (F), p represents 1 to 30, and q represents 0 to 30.)

When the compound represented by the formula (1) is any one of the compounds represented by the formulae (A) to (F), a raw material is easy to procure, and furthermore, it is possible to form lubricating layers from which superior wear resistance can be obtained and pickup can be furthermore suppressed in spite of a thin thickness, which is preferable.

The number-average molecular weight (Mn) of the fluorine-containing ether compound of the present embodiment is preferably within a range of 500 to 10000. When the number-average molecular weight is 500 or more, the evaporation of lubricants containing the fluorine-containing ether compound of the present embodiment is less likely to occur, and it is possible to prevent lubricants from being evaporated and transferred to a magnetic head. The number-average molecular weight of the fluorine-containing ether compound is more preferably 1000 or more. In addition, when the number-average molecular weight is 10000 or less, the viscosity of the fluorine-containing ether compound becomes appropriate, and it is possible to easily form lubricating layers having a thin thickness by applying lubricants containing the fluorine-containing ether compound. The number-average molecular weight of the fluorine-containing ether compound is preferably 3000 or less in order to obtain a viscosity that makes lubricants to which the fluorine-containing ether compound is applied easily handleable.

The number-average molecular weight (Mn) of the fluorine-containing ether compound is a value measured by $^1$H-NMR and $^{19}$F-NMR, specifically, $^1$H-NMR and $^{19}$F-NMR with AVANCE III400 manufactured by Bruker BioSpin Group. In the nuclear magnetic resonance (NMR) measurement, a specimen is diluted with a single or mixed solvent of hexafluorobenzene, acetone-d, tetrahydrofuran-d and the like and used in the measurement. As the reference of the $^{19}$F-NMR chemical shift, the peak of hexafluorobenzene was set to −164.7 ppm, and, as the reference of the $^1$H-NMR chemical shift, the peak of acetone was set to 2.2 ppm.

"Production Method"

A method for producing the fluorine-containing ether compound of the present embodiment is not particularly limited, and the fluorine-containing ether compound can be produced using a well-known conventional production method. The fluorine-containing ether compound of the present embodiment can be produced using, for example, a production method to be described below.

First, an addition reaction of an aliphatic hydrocarbon diepoxide having 6 to 10 carbon atoms with a compound having a perfluoropolyether chain corresponding to $R^1$ in the formula (1), which has a hydroxylmethyl group at both ends, is conducted. This generates a compound represented by a formula (1-1).

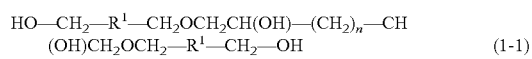

(In the formula (1-1), n is an integer of 2 to 6, and $R^1$ is the same as in the formula (1).)

Examples of the aliphatic hydrocarbon diepoxide having 6 to 10 carbon atoms that is used in the addition reaction include 1,5-hexadiene diepoxide, 1,6-heptadiene diepoxide, 1,7-octadiene diepoxide, 1,8-nonadiene diepoxide, 1,9-decadiene diepoxide and the like.

Next, the compound represented by the formula (1-1) and epichlorohydrin or epibromohydrin are reacted with each other, thereby generating perfluoropolyether having an epoxy group at both ends thereof. Furthermore, the perfluoropolyether having an epoxy group at both ends thereof and any one selected from ethylene glycol, 1,3-propanediol and 1,4-butanediol are reacted with each other. A compound obtained as described above can be separated using, for example, a method in which column chromatography is used.

The fluorine-containing ether compound represented by the formula (1) can be obtained by the above-described method.

The fluorine-containing ether compound of the present embodiment is a compound represented by the formula (1). Therefore, when a lubricating layer is formed on a protective layer using a lubricant containing this fluorine-containing ether compound, the surface of the protective layer is coated with the two PFPE chains represented by $R^1$ in the formula (1), and a friction force between a magnetic head and the protective layer is reduced. In addition, in the lubricating layer formed using the lubricant containing the fluorine-containing ether compound of the present embodiment, excellent coatability and wear resistance can be obtained, as the distance between the hydroxy groups included in the two linking groups (—CH(OH)CH$_2$OCH$_2$—) is appropriate and each linking group includes an ether bond (—O—).

In addition, the fluorine-containing ether compound of the present embodiment is closely attached onto the protective layer due to bonds between the two hydroxy groups that are included in each of the two terminal groups represented by $R^2$ and the protective layer. Furthermore, the two hydroxy groups that are included in the terminal group represented by $R^2$ bond to different carbon atoms, and the carbon atoms to which the hydroxy groups bond are bonded to each other through a linking group including an oxygen atom. Therefore, the lubricating layer containing the fluorine ether compound of the present embodiment has favorable flexibility. Therefore, the lubricating layer containing the fluorine ether compound of the present embodiment is easily adsorbed to the protective film and has excellent adhesion to the protective layer.

As described above, according to the fluorine-containing ether compound of the present embodiment, the lubricating layer and the protective layer are strongly bonded to each other, and a lubricating layer which has excellent wear resistance and can suppress pickup can be obtained.

In addition, it is possible to easily synthesize the fluorine-containing ether compound as two $R^1$ are the same and two $R^2$ are the same in the formula (1) of the fluorine-containing ether compound of the present embodiment.

[Lubricant for Magnetic Recording Medium]

A lubricant for a magnetic recording medium of the present embodiment contains the fluorine-containing ether compound represented by the formula (1).

The lubricant of the present embodiment can be used after being mixed as necessary with a well-known material that is used as a material for lubricants as long as characteristics attributed to the fluorine-containing ether compound represented by the formula (1) contained in the lubricant are not impaired.

Specific examples of a well-known material include FOMBLIN (registered trademark) ZDIAC, FOMBLIN ZDEAL, FOMBLIN AM-2001 (all manufactured by Solvay Solexis), Moresco A20H (manufactured by Moresco Corporation) and the like. The number-average molecular weight of the well-known material that is used by being mixed with the lubricant of the present embodiment is preferably 1000 to 10000.

In a case where the lubricant of the present embodiment contains a material other than the fluorine-containing ether compound represented by the formula (1), the content of the fluorine-containing ether compound represented by the formula (1) in the lubricant of the present embodiment is preferably 50 mass % or more and more preferably 70 mass % or more. The content may be 80 mass % or more, 90 mass % or more or 95 mass % or more.

The lubricant of the present embodiment contains the fluorine-containing ether compound represented by the formula (1) and is thus capable of coating the surface of protective layers at a high coating rate in spite of a thin thickness and capable of forming lubricating layers having excellent adhesion to protective layers. Therefore, according to the lubricant of the present embodiment, lubricating layers which have excellent wear resistance and can suppress pickup can be obtained in spite of a thin thickness.

[Magnetic Recording Medium]

A magnetic recording medium of the present embodiment is sequentially provided with at least a magnetic layer, a protective layer and a lubricating layer on a substrate.

In the magnetic recording medium of the present embodiment, a single underlayer or two or more underlayers can be provided as necessary between the substrate and the magnetic layer. In addition, it is also possible to provide an adhesive layer and/or a soft magnetic layer between the underlayer and the substrate.

The FIGURE is a schematic cross-sectional view showing an embodiment of the magnetic recording medium of the present invention.

A magnetic recording medium 10 of the present embodiment has a structure in which an adhesive layer 12, a soft magnetic layer 13, a first underlayer 14, a second underlayer 15, a magnetic layer 16, a protective layer 17 and a lubricating layer 18 are sequentially provided on a substrate 11.

"Substrate"

The substrate 11 can be arbitrarily selected, and it is possible to use, for example, a non-magnetic substrate or the like wherein a NiP or NiP alloy film is formed on a base made of a metal or alloy material such as Al or an Al alloy.

In addition, as the substrate 11, a non-magnetic substrate made of a non-metal material such as glass, ceramic, silicon, silicon carbide, carbon or resin may be used, and a non-magnetic substrate wherein a NiP or NiP alloy film is formed on a base made of this non-metal material may be used.

"Adhesive Layer"

The adhesive layer 12 prevents the progress of corrosion of the substrate 11 which may occur in a case where the substrate 11 and the soft magnetic layer 13, which is provided on the adhesive layer 12, are disposed in direct contact with each other.

The material of the adhesive layer 12 can be arbitrarily selected and can be appropriately selected from, for example, Cr, a Cr alloy, Ti, a Ti alloy, CrTi, NiAl, an AlRu alloy and the like. The adhesive layer 12 can be formed by, for example, a sputtering method.

"Soft Magnetic Layer"

The soft magnetic layer 13 can be arbitrarily selected and preferably has a structure in which, for example, a first soft magnetic film, an interlayer made of a Ru film and a second soft magnetic film are sequentially laminated. That is, the soft magnetic layer 13 preferably has a structure in which the interlayer made of a Ru film is sandwiched between two soft magnetic films and thereby the soft magnetic films on and under the interlayer are antiferromagnetically coupled (AFC).

Examples of the material of the first soft magnetic film and the second soft magnetic film include a CoZrTa alloy, a CoFe alloy and the like.

To the CoFe alloy that is used for the first soft magnetic film and the second soft magnetic film, any of Zr, Ta and Nb is preferably added. This accelerates the amorphization of the first soft magnetic film and the second soft magnetic film, makes it possible to improve the orientation of the first underlayer (seed layer) and makes it possible to reduce the flying height of a magnetic head.

The soft magnetic layer 13 can be formed by, for example, a sputtering method.

"First Underlayer"

The first underlayer 14 is a layer for controlling the orientations or crystal sizes of the second underlayer 15 and the magnetic layer 16 that are provided on the first underlayer 14.

Examples of the first underlayer 14 include a Cr layer, a Ta layer, a Ru layer, an alloy layer of CrMo, CoW, CrW, CrV or CrTi, and the like.

The first underlayer 14 can be formed by, for example, a sputtering method.

"Second Underlayer"

The second underlayer 15 is a layer to control the orientation of the magnetic layer 16 to be favorable. The second underlayer 15 is preferably a Ru or Ru alloy layer.

The second underlayer 15 may be a single layer or may be composed of a plurality of layers. In a case where the second underlayer 15 is composed of a plurality of layers, all of the layers may be made of the same material or at least one layer may be made of a different material.

The second underlayer 15 can be formed by, for example, a sputtering method.

"Magnetic Layer"

The magnetic layer 16 is made of a magnetic film in which the easy magnetization axis is directed in a perpendicular or parallel direction with respect to the substrate surface. The magnetic layer 16 is a layer containing Co and Pt and may be a layer further containing an oxide and/or Cr, B, Cu, Ta, Zr or the like in order to improve SNR characteristics.

Examples of the oxide that is contained in the magnetic layer 16 include $SiO_2$, $SiO$, $Cr_2O_3$, $CoO$, $Ta_2O_3$, $TiO_2$ and the like.

The magnetic layer 16 may be composed of a single layer or may be composed of a plurality of magnetic layers made of materials with different compositions.

For example, in a case where the magnetic layer 16 is composed of three layers of a first magnetic layer, a second magnetic layer and a third magnetic layer sequentially laminated from below, the first magnetic layer is preferably a granular structure made of a material containing Co, Cr and Pt and further containing an oxide. As the oxide that is contained in the first magnetic layer, for example, oxides of Cr, Si, Ta, Al, Ti, Mg, Co or the like are preferably used. Among them, in particular, $TiO_2$, $Cr_2O_3$, $SiO_2$ and the like can be preferably used. In addition, the first magnetic layer is preferably composed of a composite oxide to which two or more oxides have been added. Among them, in particular, $Cr_2O_3$—$SiO_2$, $Cr_2O_3$—$TiO_2$, $SiO_2$—$TiO_2$ and the like can be preferably used.

The first magnetic layer may contain, in addition to Co, Cr, Pt and the oxide, one or more elements selected from B, Ta, Mo, Cu, Nd, W, Nb, Sm, Tb, Ru and Re.

For the second magnetic layer, the same material as the first magnetic layer can be used. The second magnetic layer is preferably a granular structure.

The third magnetic layer preferably has a non-granular structure made of a material containing Co, Cr and Pt but containing no oxides. The third magnetic layer may contain, in addition to Co, Cr, and Pt, one or more elements selected from B, Ta, Mo, Cu, Nd, W, Nb, Sm, Tb, Ru, Re and Mn.

In a case where the magnetic layer 16 is formed of a plurality of magnetic layers, a non-magnetic layer is preferably provided between the magnetic layers adjacent to each other. In a case where the magnetic layer 16 is composed of three layers of the first magnetic layer, the second magnetic layer and the third magnetic layer, it is preferable to provide a non-magnetic layer between the first magnetic layer and the second magnetic layer and a non-magnetic layer between the second magnetic layer and the third magnetic layer.

For the non-magnetic layer that is provided between the magnetic layers adjacent to each other in the magnetic layer 16, it is possible to preferably use, for example, Ru, a Ru alloy, a CoCr alloy, a CoCrX1 alloy (X1 represents one or more elements selected from Pt, Ta, Zr, Re, Ru, Cu, Nb, Ni, Mn, Ge, Si, O, N, W, Mo, Ti, V and B) and the like.

For the non-magnetic layer that is provided between the magnetic layers adjacent to each other in the magnetic layer 16, an alloy material containing an oxide, a metallic nitride or a metallic carbide is preferably used. Specifically, as the oxide, for example, $SiO_2$, $Al_2O_3$, $Ta_2O_5$, $Cr_2O_3$, $MgO$, $Y_2O_3$, $TiO_2$ and the like can be used. As the metallic nitride, for example, $AlN$, $Si_3N_4$, $TaN$, $CrN$ and the like can be used. As the metallic carbide, for example, $TaC$, $BC$, $SiC$ and the like can be used.

The non-magnetic layer can be formed by, for example, a sputtering method.

The magnetic layer 16 is preferably a magnetic layer of perpendicular magnetic recording in which the easy magnetization axis is directed in a perpendicular direction with respect to the substrate surface in order to realize a higher recording density. The magnetic layer 16 may be a magnetic layer of longitudinal magnetic recording.

The magnetic layer 16 may be formed by any well-known conventional method such as a deposition method, an ion beam sputtering method or a magnetron sputtering method. The magnetic layer 16 is normally formed by a sputtering method.

"Protective Layer"

The protective layer 17 protects the magnetic layer 16. The protective layer 17 may be composed of a single layer or may be composed of a plurality of layers. As the material of the protective layer 17, carbon, nitrogen-containing carbon, silicon carbide and the like can be exemplified.

As the protective layer 17, a carbon-based protective layer can be preferably used, and, in particular, an amorphous carbon protective layer is preferred. When the protective layer 17 is a carbon-based protective layer, the interaction with the hydroxy groups that are included in the fluorine-containing ether compound in the lubricating layer 18 is further enhanced, which is preferable.

The adhesive force between the carbon-based protective layer and the lubricating layer 18 can be controlled by forming the carbon-based protective layer with hydrogenated carbon and/or nitrogenated carbon and adjusting the hydrogen content and/or the nitrogen content in the carbon-based protective layer. The hydrogen content in the carbon-based protective layer is preferably 3 to 20 atom % when measured by the hydrogen forward scattering method (HFS). In addition, the nitrogen content in the carbon-based protective layer is preferably 4 to 15 atom % when measured by X-ray photoelectron spectroscopy (XPS).

The hydrogen and/or nitrogen that are contained in the carbon-based protective layer do not need to be uniformly contained throughout the entire carbon-based protective layer. The carbon-based protective layer is preferably formed as a composition gradient layer in which nitrogen is contained in the lubricating layer 18 side of the protective layer 17 and hydrogen is contained in the magnetic layer 16 side of the protective layer 17. In this case, the adhesive forces between the magnetic layer 16 and the carbon-based protective layer and between the lubricating layer 18 and the carbon-based protective layer further improve.

The film thickness of the protective layer 17 is preferably set to 1 nm to 7 nm. When the film thickness of the protective layer 17 is 1 nm or more, the performance of the protective layer 17 can be sufficiently obtained. The film thickness of the protective layer 17 is preferably 7 nm or less from the viewpoint of reduction in the thickness of the protective layer 17.

As a method for forming the protective layer 17, it is possible to use a sputtering method in which a carbon-containing target material is used, a chemical vapor deposition (CVD) method in which a hydrocarbon raw material such as ethylene or toluene is used, an ion beam deposition (TBD) method and the like.

In the case of forming the carbon-based protective layer as the protective layer 17, the carbon-based protective layer can be formed by, for example, a DC magnetron sputtering method. Particularly, in the case of forming the carbon-based protective layer as the protective layer 17, an amorphous carbon protective layer is preferably formed by a plasma CVD method. The amorphous carbon protective layer formed by the plasma CVD method has a uniform surface with small roughness.

"Lubricating Layer"

The lubricating layer 18 prevents contamination of the magnetic recording medium 10. In addition, the lubricating layer 18 reduces a friction force of a magnetic head of a magnetic recording/reproducing device, which slides on the magnetic recording medium 10, and thereby improves the durability of the magnetic recording medium 10.

The lubricating layer 18 is formed in contact with the protective layer 17 as shown in the FIGURE. The lubricating layer 18 contains the above-described fluorine-containing ether compound.

In a case where the protective layer 17, which is disposed below the lubricating layer 18, is the carbon-based protective layer, the lubricating layer 18 is bonded to the protective layer 17 with a particularly high bonding force. As a result, it becomes easy to obtain the magnetic recording medium 10 in which the surface of the protective layer 17 is coated with the lubricating layer 18 at a high coating rate in spite of a thin thickness thereof, and it is possible to effectively prevent contamination on the surface of the magnetic recording medium 10.

The average film thickness of the lubricating layer 18 can be arbitrarily selected, but is preferably 0.5 nm (5 Å) to 3 nm (30 Å) and more preferably 0.5 nm (5 Å) to 1 nm (10 Å). When the average film thickness of the lubricating layer 18 is 0.5 nm or more, the lubricating layer 18 does not become an island shape or a mesh shape and is formed in a uniform film thickness. Therefore, the surface of the protective layer 17 can be coated with the lubricating layer 18 at a high coating rate. In addition, when the average film thickness of the lubricating layer 18 is 3 nm or less, it is possible to sufficiently reduce the thickness of the lubricating layer 18 and to sufficiently decrease the flying height of a magnetic head.

In a case where the surface of the protective layer 17 is not sufficiently coated with the lubricating layer 18 at a high coating rate, an environmental substance adsorbed to the surface of the magnetic recording medium 10 passes through voids in the lubricating layer 18 and intrudes into the layer below the lubricating layer 18. The environmental substance that has intruded into the layer below the lubricating layer 18 is adsorbed and bonded to the protective layer 17 and generates a contamination substance. In addition, at the time of reproducing magnetic records, this contamination substance (aggregated component) adheres (transfers) to a magnetic head as a smear to break the magnetic head or degrade the magnetic recording/reproducing characteristics of magnetic recording/reproducing devices.

Examples of the environmental substance that generates the contamination substance include a siloxane compound (cyclic siloxane or linear siloxane), an ionic impurity, a hydrocarbon having a relatively high molecular weight such as octacosane, a plasticizer such as dioctyl phthalate and the like. Examples of a metal ion that is contained in the ionic impurity include a sodium ion, a potassium ion and the like. Examples of an inorganic ion that is contained in the ionic impurity include a chlorine ion, a bromine ion, a nitrate ion, a sulfate ion, an ammonium ion and the like. Examples of an organic ion that is contained in the ionic impurity include an oxalate ion, a formate ion and the like.

"Method for Forming Lubricating Layer"

Examples of a method for forming the lubricating layer 18 include a method in which a magnetic recording medium that is not yet fully manufactured and thus includes the individual layers up to the protective layer 17 formed on the substrate 11 is prepared and a solution for forming the lubricating layer is applied and dried on the protective layer 17.

The solution for forming the lubricating layer can be obtained by dispersing and dissolving the lubricant for a magnetic recording medium of the above-described embodiment in a solvent that is arbitrarily selected as necessary and adjusting the viscosity and concentration to be suitable for the application method.

Examples of the solvent that is used for the solution for forming the lubricating layer include a fluorine-based solvent such as VERTREL (registered trademark) XF (trade name, manufactured by Dupont-Mitsui Fluorochemicals Co., Ltd.) and the like.

A method for applying the solution for forming the lubricating layer is not particularly limited, and examples thereof include a spin coating method, a spraying method, a paper coating method, a dipping method and the like.

In the case of using the dipping method, it is possible to use, for example, a method to be described below. First, the substrate 11 on which the individual layers up to the protective layer 17 have been formed is immersed into the solution for forming the lubricating layer contained in an immersion vessel of a dip coater. Next, the substrate 11 is lifted from the immersion vessel at a predetermined speed. As a result, the solution for forming the lubricating layer is applied to the surface on the protective layer 17 of the substrate 11.

The use of the dipping method makes it possible to uniformly apply the solution for forming the lubricating layer to the surface of the protective layer 17 and makes it possible to form the lubricating layer 18 on the protective layer 17 in a uniform film thickness.

In the present embodiment, a thermal treatment is preferably carried out on the substrate 11 on which the lubricating layer 18 has been formed. The thermal treatment improves the adhesion between the lubricating layer 18 and the protective layer 17 and improves the adhesive force between the lubricating layer 18 and the protective layer 17. The thermal treatment temperature is preferably set to 100° C. to 180° C. When the thermal treatment temperature is 100° C. or higher, an effect that improves the adhesion between the lubricating layer 18 and the protective layer 17 can be sufficiently obtained. In addition, when the thermal treatment temperature is set to 180° C. or lower, it is possible to prevent thermal decomposition of the lubricating layer 18. The thermal treatment time is preferably set to 10 to 120 minutes.

In the present embodiment, a treatment of irradiating the lubricating layer 18 on the substrate 11 before the thermal treatment or after the thermal treatment with ultraviolet rays (UV) may be carried out in order to further improve the adhesive force of the lubricating layer 18 to the protective layer 17.

The magnetic recording medium 10 of the present embodiment is sequentially provided with at least the magnetic layer 16, the protective layer 17 and the lubricating layer 18 on the substrate 11. In the magnetic recording medium 10 of the present embodiment, the lubricating layer 18 containing the above-described fluorine-containing ether compound is formed on the protective layer 17 to be in contact with the protective layer 17. This lubricating layer 18 coats the surface of the protective layer 17 at a high coating rate in spite of a thin thickness. Therefore, in the magnetic recording medium 10 of the present embodiment, intrusion of an environmental substance that generates a contamination substance such as an ionic impurity through voids in the lubricating layer 18 is prevented. Therefore, only a small amount of a contamination substance is present on the surface of the magnetic recording medium 10 of the present embodiment. In addition, in the lubricating layer 18 in the magnetic recording medium 10 of the present embodiment, foreign matter (smear) is less likely to be generated, and pickup can be suppressed. In addition, the lubricating layer 18 in the magnetic recording medium 10 of the present embodiment has excellent wear resistance. Therefore, the magnetic recording medium 10 of the present embodiment has excellent reliability and durability.

EXAMPLES

Hereinafter, the present invention will be more specifically described using examples and comparative examples. The present invention is not limited only to the following examples.

Example 1

A compound represented by the following formula (5) was produced by a method to be described below.

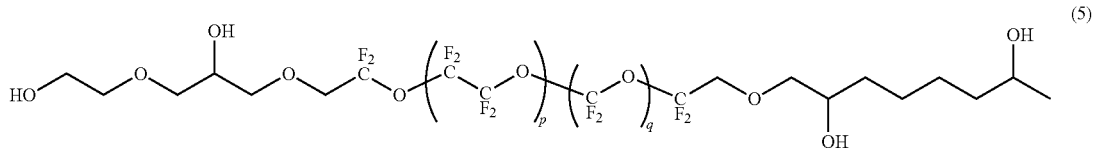

(5)

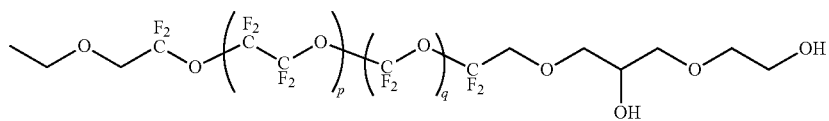

(In the formula (5), p is 4.5 and q is 4.5.)

A compound represented by $HOCH_2CF_2O(CF_2CF_2O)_p(CF_2O)_qCF_2CH_2OH$ (in the formula, p is 4.5 and q is 4.5) (number-average molecular weight: 1000, molecular weight distribution: 1.1) (30.0 g), 1,7-octadiene diepoxide (0.57 g) (molecular weight: 142.2, 4.0 mmol) and t-BuOH (10 mL) were charged into a 100 mL eggplant flask in a nitrogen gas atmosphere and stirred at room temperature until the components became homogeneous. t-BuOK (0.35 g) (molecular weight: 112.21, 3.1 mmol) was added to this homogeneous liquid and stirred at 70° C. for 16 hours to be reacted.

An obtained reaction product was cooled to 25° C., moved to a separatory funnel containing water (40 mL) and extracted twice with ethyl acetate (100 mL). An organic layer was washed with water and dehydrated with anhydrous sodium sulfate as a drying agent. The drying agent was filtered, the filtrate was then concentrated, and the residue was purified by silica gel column chromatography, thereby obtaining a compound represented by the following formula (6) (5.50 g) (number average molecular weight: 2136, 2.5 mmol).

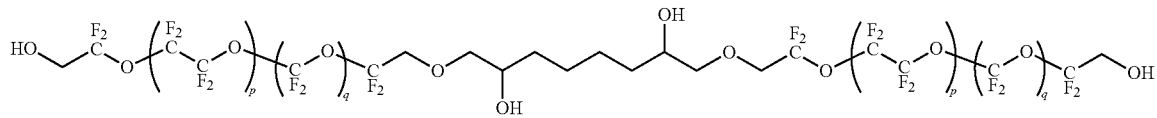

(6)

(In the formula (6), p is 4.5 and q is 4.5.)

Next, the compound represented by the formula (6) (5.00 g), epibromohydrin (0.64 g) (molecular weight: 137.0, 4.7 mmol) and t-BuOH (20 mL) were charged into an eggplant flask and stirred at room temperature until the components became homogeneous. t-BuOK (0.53 g) (molecular weight: 112.2, 4.7 mmol) was added to this homogeneous liquid and stirred at 70° C. for six hours to be reacted.

An obtained reaction product was cooled to 25° C., moved to a separatory funnel containing water (30 mL) and extracted twice with ethyl acetate (80 mL). An organic layer thereof was washed with water and dehydrated with anhydrous sodium sulfate. The drying agent was filtered, the filtrate was then concentrated, and the residue was purified by silica gel column chromatography, thereby obtaining a compound represented by the following formula (7) (4.3 g) (number average molecular weight: 2248, 1.9 mmol).

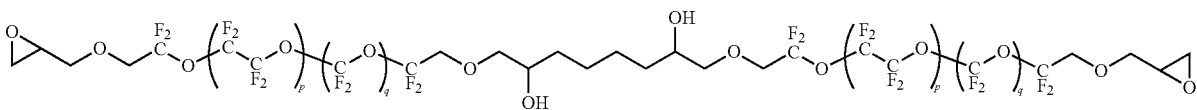

(7)

(In the formula (7), p is 4.5 and q is 4.5.)

Next, the compound represented by the formula (7) (4.0 g), ethylene glycol (1.1 g) (molecular weight: 62.1, 17.7 mmol) and t-BuOH (30 mL) were charged into an eggplant flask and stirred at room temperature until the components became homogeneous. t-BuOK (0.16 g) (molecular weight: 112.2, 1.4 mmol) was added to this homogeneous liquid and stirred at 70° C. for six hours to be reacted.

An obtained reaction product was cooled to 25° C., moved to a separatory funnel containing water (30 mL) and extracted twice with ethyl acetate (80 mL). An organic layer thereof was washed with water and dehydrated with anhydrous sodium sulfate. The drying agent was filtered, the filtrate was then concentrated, and the residue was purified by silica gel column chromatography, thereby obtaining a compound represented by the above-described formula (5) (3.2 g).

$^1$H-NMR and $^{19}$F-NMR measurement was carried out on the obtained compound (5), and the structure was identified from the following results.

(Identification Data)

$^1$H-NMR (acetone-$D_6$): δ [ppm] 1.00 to 1.40 (8H), 3.30 to 4.20 (32H)

$^{19}$F-NMR (acetone-$D_6$): δ [ppm]=−55.5 to −51.5 (18F), −78.5 (4F), −80.5 (4F), −91.0 to −88.5 (36F)

Example 2

A compound represented by the following formula (8) (3.5 g) was obtained in the same manner as in Example 1 except that fluoropolyether represented by $HOCH_2CF_2O(CF_2CF_2O)_p(CF_2O)_qCF_2CH_2OH$ (in the formula, p is 7.0 and q is 0) (number-average molecular weight: 1000, molecular weight distribution: 1.1) was used in place of the fluoropolyether represented by $HOCH_2CF_2O(CF_2CF_2O)_p(CF_2O)_qCF_2CH_2OH$ used in Example 1 (in the formula, p is 4.5 and q is 4.5).

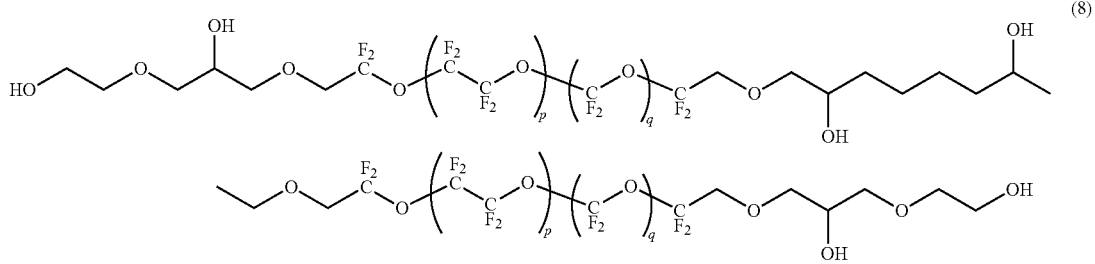

(8)

(In the formula (8), p is 7.0 and q is 0.)

$^1$H-NMR and $^{19}$F-NMR measurement was carried out on the obtained compound (8), and the structure was identified from the following results.

(Identification Data)

$^1$H-NMR (acetone-D$_6$): δ [ppm] 1.00 to 1.40 (8H), 3.30 to 4.20 (32H)

$^{19}$F-NMR (acetone-D$_6$): δ [ppm]=−78.5 (4F), −81.3 (4F), −90.0 to −88.5 (56F)

Example 3

A compound represented by the following formula (9) (3.2 g) was obtained in the same manner as in Example 1 except that fluoropolyether represented by HOCH$_2$CF$_2$CF$_2$O(CF$_2$CF$_2$CF$_2$O)$_r$CF$_2$CF$_2$CH$_2$OH (in the formula, r is 4.5) (number-average molecular weight: 1000, molecular weight distribution: 1.1) was used in place of the fluoropolyether represented by HOCH$_2$CF$_2$O(CF$_2$CF$_2$O)$_p$(CF$_2$O)$_q$CF$_2$CH$_2$OH used in Example 1 (in the formula, p is 4.5 and q is 4.5).

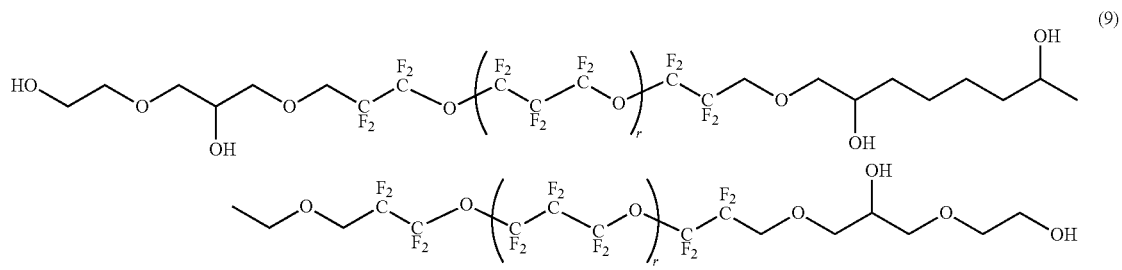

(9)

(In the formula (9), r is 4.5.)

$^1$H-NMR and $^{19}$F-NMR measurement was carried out on the obtained compound (9), and the structure was identified from the following results.

(Identification Data)

$^1$H-NMR (acetone-D$_6$): δ [ppm] 1.00 to 1.40 (8H), 3.30 to 4.20 (32H)

$^{19}$F-NMR (acetone-D$_6$): δ [ppm]=−84.0 to −83.0 (36F), −86.4 (8F), −124.3 (8F), −130.0 to −129.0 (18F)

Example 4

A compound represented by the following formula (10) (3.2 g) was obtained in the same manner as in Example 1 except that fluoropolyether represented by HOCH$_2$CF$_2$CF$_2$CF$_2$O(CF$_2$CF$_2$CF$_2$CF$_2$O)$_s$CF$_2$CF$_2$CF$_2$CH$_2$OH (in the formula, s is 3.0) (number-average molecular weight: 1000, molecular weight distribution: 1.1) was used in place of the fluoropolyether represented by HOCH$_2$CF$_2$O(CF$_2$CF$_2$O)$_p$(CF$_2$O)$_q$CF$_2$CH$_2$OH used in Example 1 (in the formula, p is 4.5 and q is 4.5).

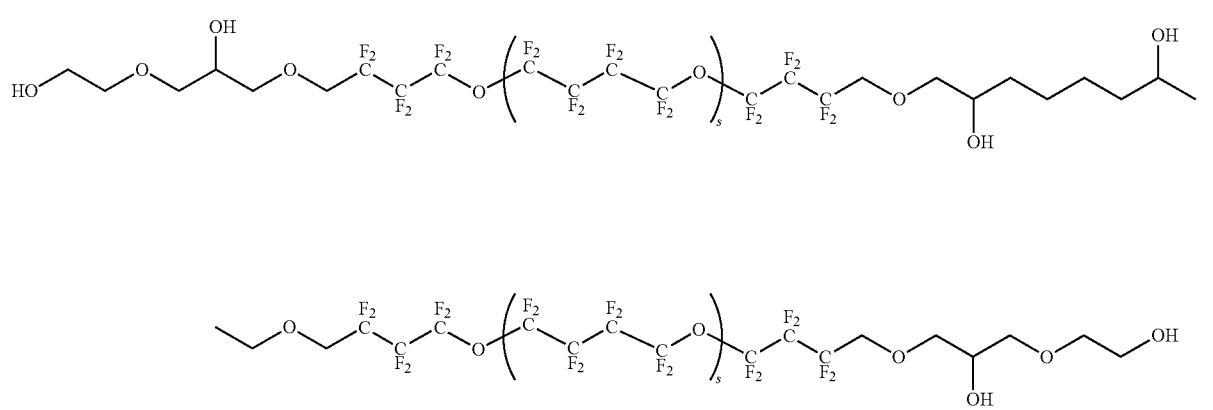

(10)

(In the formula (10), s is 3.0.)
$^1$H-NMR and $^{19}$F-NMR measurement was carried out on the obtained compound (10), and the structure was identified from the following results.
(Identification Data)
$^1$H-NMR (acetone-$D_6$): δ [ppm] 1.00 to 1.40 (8H), 3.30 to 4.20 (32H)
$^{19}$F-NMR (acetone-$D_6$): δ [ppm]=−84.0 to −83.0 (32F), −122.5 (8F), −126.0 (24F), −129.0 to −128.0 (8F)

Example 5

A compound represented by the following formula (11) (3.5 g) was obtained in the same manner as in Example 1 except that 1,9-decadiene diepoxide was used in place of 1,7-octadiene diepoxide used in Example 1.

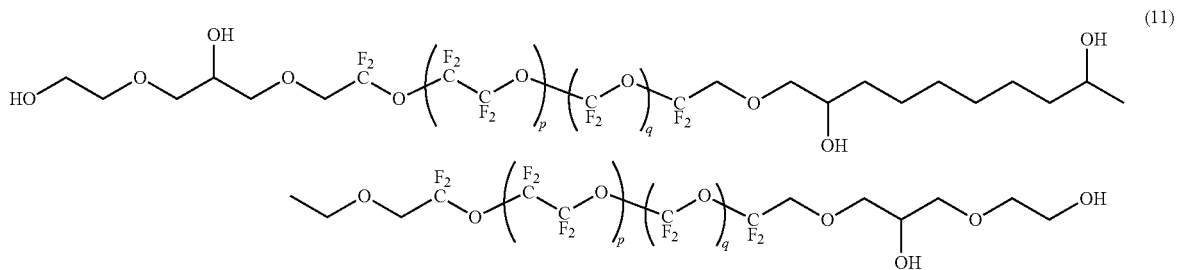

(In the formula (11), p is 4.5 and q is 4.5.)
$^1$H-NMR and $^{19}$F-NMR measurement was carried out on the obtained compound (11), and the structure was identified from the following results.
(Identification Data)
$^1$H-NMR (acetone-$D_6$): δ [ppm] 1.00 to 1.40 (12H), 3.20 to 4.20 (32H)
$^{19}$F-NMR (acetone-$D_6$): δ [ppm]=−55.5 to −51.5 (18F), −78.5 (4F), −80.5 (4F), −91.0 to −88.5 (36F)

Example 6

A compound represented by the following formula (12) (3.4 g) was obtained in the same manner as in Example 1 except that 1,3-propanediol was used in place of ethylene glycol used in Example 1.

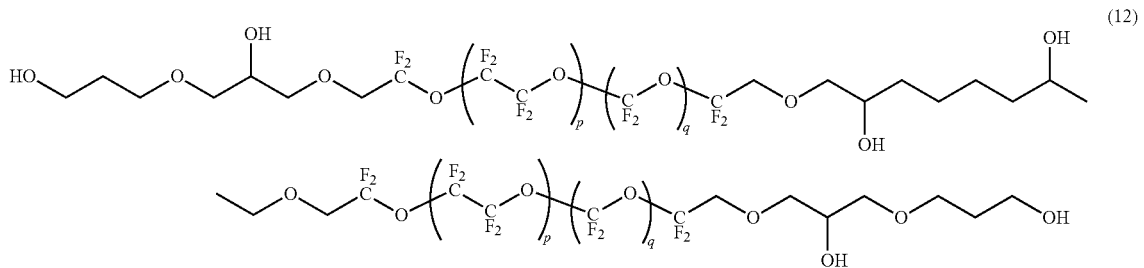

(In the formula (12), p is 4.5 and q is 4.5.)
$^1$H-NMR and $^{19}$F-NMR measurement was carried out on the obtained compound (12), and the structure was identified from the following results.
(Identification Data)
$^1$H-NMR (acetone-$D_6$): δ [ppm] 1.00 to 1.40 (12H), 3.30 to 4.20 (32H)
$^{19}$F-NMR (acetone-$D_6$): δ [ppm]=−55.5 to −51.5 (18F), −78.5 (4F), −80.5 (4F), −91.0 to −88.5 (36F)

Example 7

A compound represented by the following formula (13) (3.4 g) was obtained in the same manner as in Example 1 except that 1,4-butanediol was used in place of ethylene glycol used in Example 1.

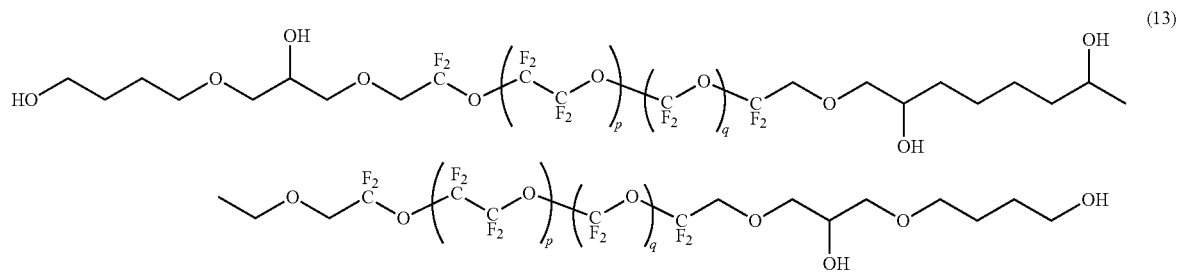

(13)

(In the formula (13), p is 4.5 and q is 4.5.)

$^1$H-NMR and $^{19}$F-NMR measurement was carried out on the obtained compound (13), and the structure was identified from the following results.

(Identification Data)

$^1$H-NMR (acetone-$D_6$): δ [ppm] 1.00 to 1.40 (16H), 3.30 to 4.20 (32H)

$^{19}$F-NMR (acetone-$D_6$): δ [ppm]=−55.5 to −51.5 (18F), −78.5 (4F), −80.5 (4F), −91.0 to −88.5 (36F)

Comparative Example 1

Fomblin Z-tetraol manufactured by Solvay Solexis that is represented by the following formula (14) was used.

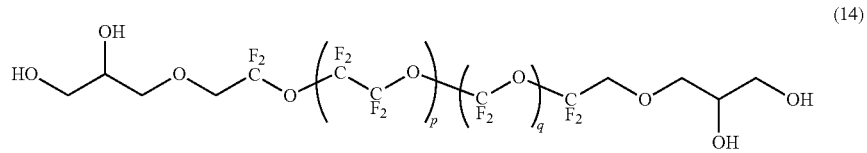

(14)

(In the formula (14), p is 9.0 and q is 9.0.)

Comparative Example 2

A compound represented by the following formula (15) was synthesized by the method described in Patent Document 1.

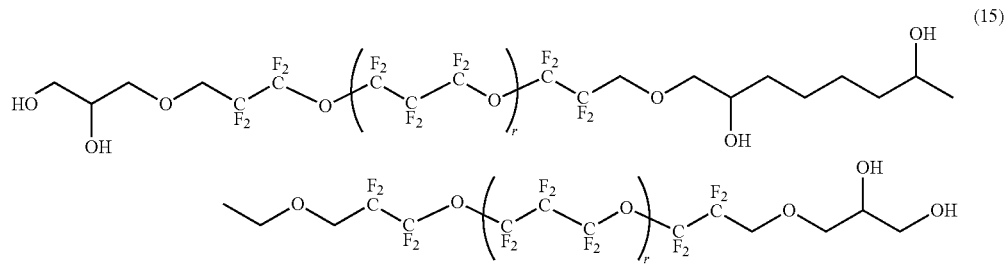

(15)

(In the formula (15), r is 4.5.)

Comparative Example 3

A compound represented by the following formula (16) was synthesized by the method described in Patent Document 2.

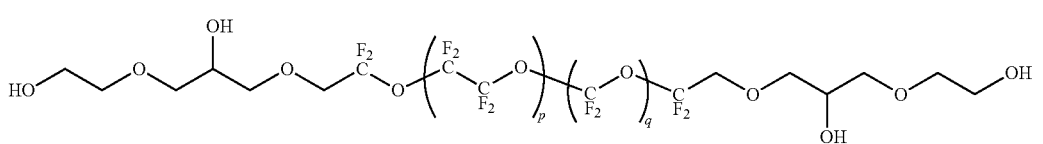

(16)

(In the formula (16), p is 9.0 and q is 9.0.)

The number-average molecular weights of the compounds of Examples 1 to 7 and Comparative Examples 1 to 3 obtained as described above were obtained by the above-described $^1$H-NMR and $^{19}$F-NMR measurement. The results are shown in Table

TABLE 1

| | Compound | Number-average molecular weight |
|---|---|---|
| Example 1 | (5) | 2372 |
| Example 2 | (8) | 2358 |
| Example 3 | (9) | 2428 |
| Example 4 | (10) | 2430 |
| Example 5 | (11) | 2400 |
| Example 6 | (12) | 2400 |
| Example 7 | (13) | 2429 |
| Comparative Example 1 | (14) | 1964 |
| Comparative Example 2 | (15) | 2240 |
| Comparative Example 3 | (16) | 2052 |

Next, solutions for forming a lubricating layer were prepared using the compounds obtained in Examples 1 to 7 and Comparative Examples 1 to 3 by a method to be described below. In addition, lubricating layers of magnetic recording media were formed using the obtained solutions for forming a lubricating layer by a method to be described below, and magnetic recording media of Examples 1 to 7 and Comparative Examples 1 to 3 were obtained.

"Solutions for Forming Lubricating Layer"

The compounds obtained in Examples 1 to 7 and Comparative Examples 1 to 3 were dissolved in VERTREL (registered trademark) XF (trade name, manufactured by Dupont-Mitsui Fluorochemicals Co., Ltd.), which is a fluorine-based solvent, diluted with VERTREL XF, such that the film thicknesses became 9 Å to 10 Å when applied onto protective layers, and used as solutions for forming a lubricating layer.

"Magnetic Recording Media"

Magnetic recording media each having an adhesive layer, a soft magnetic layer, a first underlayer, a second underlayer, a magnetic layer and a protective layer sequentially provided on a substrate having a diameter of 65 mm were prepared. As the protective layer, a carbon layer was used.

The solutions for forming a lubricating layer of Examples 1 to 7 and Comparative Examples 1 to 3 were applied onto the protective layers of the magnetic recording media, in which the individual layers up to the protective layer had been formed, by the dipping method. The dipping method was carried out under conditions of an immersion speed of 10 mm/sec, an immersion time of 30 seconds and a lifting speed of 1.2 mm/sec.

After that, the magnetic recording media to which the solutions for forming a lubricating layer had been applied were put into a thermostatic chamber (120° C.) and heated for 10 minutes to remove the solvent in the solutions for forming a lubricating layer, thereby forming lubricating layers on the protective layers and obtaining magnetic recording media.

The film thicknesses of the lubricating layers in the magnetic recording media of Examples 1 to 7 and Comparative Examples 1 to 3 obtained as described above were measured using FT-IR (trade name: Nicolet iS50, manufactured by Thermo Fisher Scientific). The results are shown in Table 2.

In addition, measurement of adhesion (bonding ratio) between lubricating layer and protective layer, a wear resistance test, and a pickup suppression test were carried out as described below on the magnetic recording media of Examples 1 to 7 and Comparative Examples 1 to 3.

(Measurement of Adhesion (Bonding Ratio) Between Lubricating Layer and Protective Layer)

The magnetic recording medium in which a lubricating layer had been formed was washed using a method in which the magnetic recording medium was immersed in Vertrel XF as a solvent for 10 minutes and then withdrawn from the solvent. Immersion of the magnetic recording medium in the solvent was performed at a speed of 10 mm/sec, whereas the withdrawal speed was 1.2 mm/sec.

Subsequently, using the same method as that used for measuring the film thickness of the lubricating layer prior to the washing, the film thickness of the lubricating layer was measured.

Then, the film thickness of the lubricating layer prior to washing was deemed A, the film thickness of the lubricating layer after washing (after solvent immersion) was deemed B, and the binding ratio (bonding ratio) of the lubricant was calculated from a ratio between A and B ((B/A)×100(%)). Using the calculated bonding ratio, the adhesion between the lubricating layer and the protective layer was evaluated against the criteria listed below.

[Evaluation of Adhesion (Bonding Ratio)]

A (Favorable): bonding ratio of 65% or higher

B (Permissible): bonding ratio of 50% or higher and less than 65%

C (Impermissible): bonding ratio of less than 50%

(Wear Resistance Test)

An alumina sphere having a diameter of 2 mm, which was a contact, was slid on the lubricating layers of the magnetic recording media using a pin-on disc-type friction wear tester at a load of 40 gf and a sliding speed of 0.25 m/sec, and the friction coefficients of the surfaces of the lubricating layers were measured. In addition, the sliding times until the friction coefficients of the surfaces of the lubricating layers sharply increased were measured. The sliding time until the friction coefficient sharply increased was measured four times for the lubricating layer of each magnetic recording medium, and the average value (time) was used as an index of the wear resistance of a lubricant coating.

The results of the magnetic recording media of Examples 1 to 7 and Comparative Examples 1 to 3 are shown in Table 2. Evaluation of the wear resistance by the sliding time until the friction coefficient sharply increased was carried out as described below.

[Evaluation of Wear Resistance (Sliding Time)]

AA (Excellent): 650 seconds or longer

A (Favorable): 550 seconds or longer and shorter than 650 seconds

B (Permissible): 450 seconds or longer and shorter than 550 seconds

C (impermissible): Shorter than 450 seconds

The time until the friction coefficient sharply increased can be used as an index of the wear resistance of the lubricating layers for the reason to be described below. The lubricating layers of the magnetic recording media are getting worn due to the use of the magnetic recording media. This is because, once the lubricating layer disappears due to friction, the contact and the protective layer come into direct contact with each other and the friction coefficient sharply increases. The time until the friction coefficient sharply increased is also considered to correlate with friction tests.

(Pickup Suppression Test)

The magnetic recording medium and a magnetic head were mounted on a spin stand, and the magnetic head was floated at a fixed point for 10 minutes under normal temperature and reduced pressure conditions (about 250 torr). Subsequently, the surface of the magnetic head facing the magnetic recording medium (the surface of the lubricating layer) was analyzed using an Electron Spectroscopy for Chemical Analysis (ESCA) analyzer. Based on the intensity of the fluorine-derived peak (signal intensity (a.u.)) measured by ESCA, the amount of the lubricant adhered to the magnetic head was evaluated against the criteria shown in Table 3. The smaller amount of the lubricant adhered to the magnetic head is better, and the lower signal intensity is better.

(Comprehensive Evaluation)

As comprehensive evaluation, compounds for which all results were favorable were indicated by AA (excellent), compounds for which one impermissible result was obtained were indicated by B (Permissible), and compounds for which two impermissible results were obtained were indicated by C (impermissible) in Table 2.

of Examples 1 to 7, the wear resistance was favorable compared with the magnetic recording media of Comparative Examples 1 to 3.

In more detail, in Comparative Example 1 in which a compound having a perfluoropolyether chain at the center of the molecule was used, the evaluation of the bonding ratio and the pickup suppression test were C (Impermissible), and the evaluation of the wear resistance test was B (Permissible).

In Comparative Example 2 in which a compound having perfluoropolyether chains bonded at both terminals of a hydrocarbon chain, which was located at the center of the molecule, through a linking group including a hydroxy group, the evaluation of the bonding ratio was B (Permissible), and the evaluation of the wear resistance was A (Favorable). However, the results of the bonding ratio, pickup suppression test and wear resistance thereof were inferior to that of Example 3 which used a compound wherein terminal groups represented by —$OCH_2CH(OH)CH_2O(CH_2)_mOH$ (m in the formula is an integer of 2 to 4) were bonded to the ends of the perfluoropolyether chains through a methylene group.

In Comparative Example 3 which used a compound wherein terminal groups represented by —$OCH_2CH(OH)CH_2O(CH_2)_mOH$ (m in the formula is an integer of 2 to 4) were bonded to the ends through a methylene group, the evaluation of the wear resistance was A (Favorable). However, since the compound in which the perfluoropolyether chain is located at the center of the molecule was used in Comparative Example 3, the evaluation of the bonding ratio and the pickup suppression test were C (Impermissible).

From these results, it was found that a lubricating layer which exhibits excellent adhesion to the protective layer, can

TABLE 2

| | Compound | Film thickness (Å) | Bonding Ratio % | Bonding Ratio Evaluation | Wear resistance test | Pickup Suppression Test | Comprehensive evaluation |
|---|---|---|---|---|---|---|---|
| Example 1 | (5) | 9.5 | 74 | A | AA | AA | AA |
| Example 2 | (8) | 10.0 | 69 | A | AA | AA | AA |
| Example 3 | (9) | 9.5 | 71 | A | AA | AA | AA |
| Example 4 | (10) | 10.0 | 70 | A | AA | AA | AA |
| Example 5 | (11) | 9.5 | 72 | A | AA | AA | AA |
| Example 6 | (12) | 9.0 | 74 | A | AA | AA | AA |
| Example 7 | (13) | 9.0 | 75 | A | AA | AA | AA |
| Comparative Example 1 | (14) | 9.5 | 42 | C | B | C | C |
| Comparative Example 2 | (15) | 9.5 | 61 | B | A | C | B |
| Comparative Example 3 | (16) | 9.5 | 48 | C | A | C | C |

TABLE 3

| Evaluation | Signal intensity | ESCA signal intensity |
|---|---|---|
| AA | 500 or less | There is no adhesion of lubricant to the head, and there is no change in signal intensity. |
| A | Greater than 500 and 1000 or less | Amount of lubricant adhered to the head is small, and signal intensity is low. |
| C | Greater than 1000 | Amount of lubricant adhered to the head is large, and signal intensity is high. |

As shown in Table 2, in the magnetic recording media of Examples 1 to 7, the evaluation results of the adhesion (bonding ratio) between lubricating layer and protective layer, and pickup suppression test were favorable. In addition, as shown in Table 2, in the magnetic recording media suppress pickup, and exhibits excellent wear resistance even when the thickness thereof is reduced to 9 Å to 10 Å, can be obtained by forming the lubricating layer which contains the compounds of Examples 1 to 7 on the protective layer of the magnetic recording medium.

INDUSTRIAL APPLICABILITY

The present invention provides a fluorine-containing ether compound that is capable of forming lubricating layers which have excellent wear resistance and can suppress pickup in spite of a thin thickness, and can be preferably used as a material for lubricants for magnetic recording media. The use of a lubricant for a magnetic recording medium containing the fluorine-containing ether compound of the present invention makes it possible to form lubricating layers capable of realizing excellent wear resistance and can suppress pickup, in spite of a thin thickness.

REFERENCE SIGNS LIST

10 Magnetic recording medium
11 Substrate
12 Adhesive layer
13 Soft magnetic layer
14 First underlayer
15 Second underlayer
16 Magnetic layer
17 Protective layer
18 Lubricating layer

The invention claimed is:

1. A fluorine-containing ether compound represented by any one of the following formulae (A) to (C),

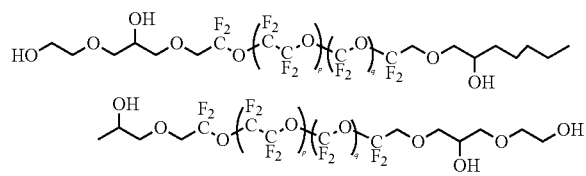
(A)

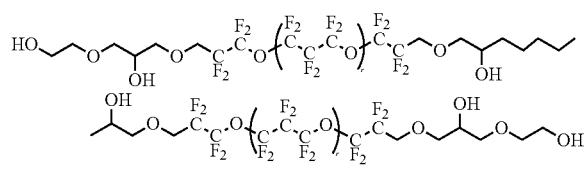
(B)

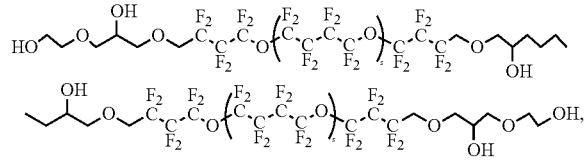
(C)

in the formula (A), p represents 1 to 30, and q represents 0 to 30,
in the formula (B), r represents 1 to 30,
in the formula (C), s represents 1 to 20.

2. The fluorine-containing ether compound according to claim 1, wherein a number-average molecular weight thereof is in a range of 500 to 10000.

3. A lubricant for a magnetic recording medium, comprising:
the fluorine-containing ether compound according to claim 1.

4. A magnetic recording medium, wherein at least a magnetic layer, a protective layer and a lubricating layer are sequentially provided on a substrate, and
the lubricating layer contains the fluorine-containing ether compound according to claim 1.

5. The magnetic recording medium according to claim 4, wherein the lubricating layer has an average film thickness of 0.5 nm to 3 nm.

6. The fluorine-containing ether compound according to claim 1, wherein in formula (A), p represents 1 to 20 and q represents 0 to 20,
in formula (B), r represents 1 to 20, and
in formula (C), s represents 1 to 15.

7. The fluorine-containing ether compound according to claim 1, wherein in formula (A), p represents 1 to 20 and q represents 0 to 20,
in formula (B), r represents 2 to 20, and
in formula (C), s represents 2 to 15.

8. The fluorine-containing ether compound according to claim 1, wherein in formula (A), p represents 1 to 15 and q represents 0 to 15,
in formula (B), r represents 2 to 20, and
in formula (C), s represents 2 to 15.

9. The fluorine-containing ether compound according to claim 1, wherein in formula (A), p represents 1 to 15 and q represents 0 to 15,
in formula (B), r represents 3 to 10, and
in formula (C), s represents 2 to 8.

10. The fluorine-containing ether compound according to claim 1, wherein in formula (A), p represents 1 to 13 and q represents 0 to 13,
in formula (B), r represents 3 to 10, and
in formula (C), s represents 2 to 8.

11. The fluorine-containing ether compound according to claim 10, wherein a number-average molecular weight thereof is in a range of 1000 to 10000.

12. The fluorine-containing ether compound according to claim 10, wherein a number-average molecular weight thereof is in a range of 500 to 3000.

13. The fluorine-containing ether compound according to claim 10, wherein a number-average molecular weight thereof is in a range of 1000 to 3000.

14. The fluorine-containing ether compound according to claim 1, wherein a number-average molecular weight thereof is in a range of 1000 to 10000.

15. The fluorine-containing ether compound according to claim 1, wherein a number-average molecular weight thereof is in a range of 500 to 3000.

16. The fluorine-containing ether compound according to claim 1, wherein a number-average molecular weight thereof is in a range of 1000 to 3000.

* * * * *